(12) United States Patent
Brady et al.

(10) Patent No.: US 7,432,397 B2
(45) Date of Patent: Oct. 7, 2008

(54) IMAGING COMPOUNDS

(75) Inventors: Frank Brady, London (GB); Sajinder Kaur Luthra, London (GB)

(73) Assignee: Hammersmith Imanet Ltd., London (GB)

( * ) Notice: Subject to any disclaimer, the term of this patent is extended or adjusted under 35 U.S.C. 154(b) by 127 days.

(21) Appl. No.: 10/522,204

(22) PCT Filed: Jul. 16, 2003

(86) PCT No.: PCT/GB03/03078

§ 371 (c)(1),
(2), (4) Date: Jan. 18, 2005

(87) PCT Pub. No.: WO2004/007440

PCT Pub. Date: Jan. 22, 2004

(65) Prior Publication Data

US 2005/0260125 A1 Nov. 24, 2005

(30) Foreign Application Priority Data

Jul. 17, 2002 (GB) ................... 0216621.3

(51) Int. Cl.
C07C 279/18 (2006.01)
A61K 51/00 (2006.01)
C07F 5/00 (2006.01)
(52) U.S. Cl. ................. 564/238; 514/634; 424/1.11
(58) Field of Classification Search ............... 585/534, 585/505; 564/238; 514/634; 424/1.11
See application file for complete search history.

(56) References Cited

FOREIGN PATENT DOCUMENTS

WO 94/27591 12/1994
WO 95/14461 6/1995

OTHER PUBLICATIONS

Gibbs, Andrew R.; Morimoto, Hiromi; VanBrocklin, Henry F.; Williams, Philip G.; Biegon, Anat. Synthesis of N-(2-chloro-5-methylthiophenyl)-N'-(3-methyl-thiophenyl)-N'-[3H3] methylguanidine Journal of Labelled Compounds and Radiopharmaceuticals (2002), 45 (5), 395-400.*
Rikki N. Waterhouse, Filip Dumont, Abida Sultana, Norman Simpson and Marc Laruelle J Label Compd Radiopharm 2002; 45: 955-964.*
Donald M Wieland, Thomas J. Mangner, Muthiah N. Inbasekaran, Lawrence E. Brown, and Jiann-long Wu J. Med. Chem. 1984,27,149-155.*
Anthony F Shields, Michael M Graham, Susan M. Kozawa, Laura B. Kozell, Jeanne M. Link J Nucl Med 1992; 33:581-584.*
Lain-Yen Hu, Junqing Guo, Sharad S Magar, James B Fischer, Kathleen J Burke-Howie and Graham J Durant J Med Chem 1997, 40, 4281-4289.*
Chyng-Yann Shiue, Shankar Vallabhahosula, Alfred P Wolf, Stephen L Dewey, Joanna S Fowler, David J Schlyer, Carroll D Arnett and Yi-Guo Zhou Nuclear Medicine and Biology, vol. 24, pp. 145-150, 1997.*
J. Owens et.al.: Nuclear Medicine & Biology, vol. 27, No. 6, 2000, pp. 557-564.
A.R. Gibbs, et.al: Journal of Labelled Compounds and Radiopharmaceuticals, vol. 45, No. 5, Apr. 2002 pp. 395-400.
A.A. Wilson, et.al.: J. Med. Chem. vol. 34, No. 6, 1991, pp. 1867-1870.
CAPLUS Abstract Accession No. 2002:370623 & Journal of Labelled Compounds & Radiopharmaceuticals vol. 45, No. 5, 2002, Andrew R Gibbs, et.al, "Synthesis of N-(2-chloro-5-methylthiophenyl)-N'-(3-methylthiophenyl)-N'-[3H3]methylguanidine, {[3H3]CNS-5161]}", pp. 395-400 [see abstract].
CAPLUS Abstract Accession No. 2002:274772 & British Journal of Clinical Pharmacology vol. 53, No. 3, 2002, MR Walters, et.al, "Early clinical experience with the novel NMDA receptor antagonist CNS 5161", pp. 305-311 (see abstract).
CAPLUS Abstract Accession No. 2001: 177402 & Biorganic & Medicinal Chemistry Letters vol. 11, No. 4, 2001, S Padmanabhan et.al., Identification and characterization of a potential ischemia-selective N-methyl-d-aspartate (NMDA) receptor ion-channel blocker, CNS 5788, pp. 501-504 (see abstract).
CAPLUS Abstract Accession No. 1998:35396 & Journal of Medicinal Chemistry vol. 40, No. 26, 1997, Lain-Yen Hu, et.al, "Synthesis and pharmacological evaluation of N-(2,5-disubstituted phenyl)-N'-(3-substituted phenyl)-N'-methylguanidines as N-methyl-D-aspartate receptor ion-channel blockers", pp. 4281-4289 (see abstract).
International Search Report for PCT/GB03/03078 dated Oct. 8, 2003.
British Search Report for GB0216621.3 dated Dec. 20, 2002.
Joannes TM Linders, Current Opinion in CPNS Investigation Drugs 1999, pp. 167-170.
Paula M. Bokesch, Anesthesiology, pp. 202-208.
A. Bigeon, et.al., Development of CNS5161 for NMDA Receptor Imaging, J. Nucl. Med. 43 (2002) No. 1447 p. 360P.

* cited by examiner

*Primary Examiner*—Shailendra Kumar
(74) *Attorney, Agent, or Firm*—Craig Bohlken

(57) ABSTRACT

The invention relates to compounds of formula: (I) or a salt or solvate thereof, wherein: $R^1$ is $-^{11}CH_2R^5$ or $[^{18}F]-C_{1-4}$ fluoroalkyl wherein $R^5$ is hydrogen or $C_{1-4}$ alkyl; $R_2$ is hydrogen or $C_{1-4}$ alkyl; $R^3$ is halo; and $R^4$ is halo, $C_{1-4}$ alkylthio, or $C_{1-4}$ alkyl; and their use for imaging central nervous system (CNS) receptors.

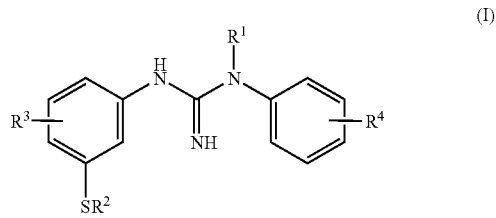

7 Claims, 1 Drawing Sheet

IMAGING COMPOUNDS

Figure 1A:
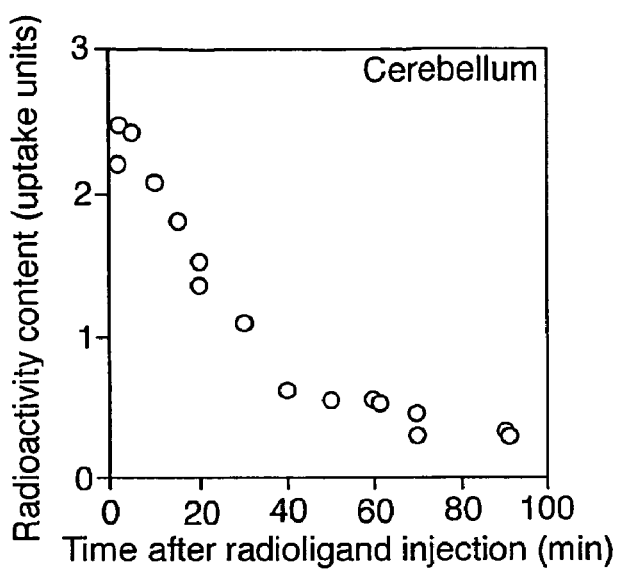

This application is a filing under 35 U.S.C 371 of international application number PCT/GB2003/003078, filed Jul. 16, 2003, which claims priority to application number 0216621.3 filed Jul. 17, 2002, in Great Britain the entire disclosure of which is hereby incorporated by reference.

The present invention relates to the field of medical imaging, in particular to positron emission tomography (PET) and single-photon emission computed tomography (SPECT) and provides compounds and methods for imaging central nervous system (CNS) receptors.

The N-methyl-D-aspartate (NMDA) receptor is one of the main subtypes of glutamatergic receptors and is widely accepted to play a pivotal role in long term depression, long term potentiation, and developmental neuronal plasticity. NMDA induced excitotoxicity that is due at least partially to overactivation or prolonged stimulation of NMDA receptors has been found in many CNS diseases such as stroke, brain or spinal chord trauma, epilepsy, Alzheimer's disease, and Huntington's disease. A number of compounds have been investigated as potential radioligands for studying the NMDA receptor ion-channel site in vivo using PET. However, the majority of these compounds have suffered the disadvantages of poor penetration of the blood brain barrier or high non-specific binding. Therefore, there exists a need for further radioligands for the NMDA receptor.

WO 94/27591 describes certain substituted guanidines and their use for therapy.

Accordingly, in one aspect of the present invention, there is provided a compound of formula (I):

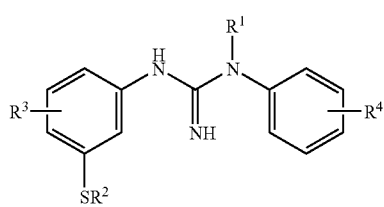

(I)

or a salt or solvate thereof, wherein:
$R^1$ is —$^{11}CH_2R^5$ or [$^{18}F$]—$C_{1-4}$fluoroalkyl wherein $R^5$ is hydrogen or $C_{1-4}$ alkyl;
$R^2$ is hydrogen or $C_{1-4}$ alkyl;
$R^3$ is halo; and
$R^4$ is halo, $C_{1-4}$ alkylthio, or $C_{1-4}$ alkyl.

$R^1$ is, in one aspect, preferably —$^{11}CH_3$, —$^{11}CH_2CH_3$, or —$^{11}CH_2CH_2CH_3$, and is most preferably —$^{11}CH_3$.

In an alternative aspect, $R^1$ is preferably —$CH_2^{18}F$, —$CH_2CH_2^{18}F$, or —$CH_2CH_2CH_2^{18}F$, and is most preferably —$CH_2^{18}F$.

$R^2$ is preferably methyl.

$R^3$ is preferably attached to the phenyl ring in the para-position relative to the group —$SR^2$, and in a preferred aspect, $R^3$ is chloro.

$R^4$ is preferably attached to the phenyl ring in the meta-position relative to the guanidine bridge, and in a preferred aspect, $R^4$ is $C_{1-4}$ alkylthio, more preferably —$SCH_3$.

Thus, in a preferred aspect of the invention, there is provided a compound of formula (Ia):

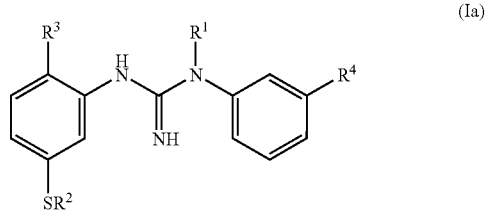

(Ia)

or a salt or solvate thereof, wherein $R^1$, $R^2$, $R^3$, and $R^4$ are as defined for the compounds of formula (I).

In a more preferred aspect of the invention, there is provided a compound of formula (Ib):

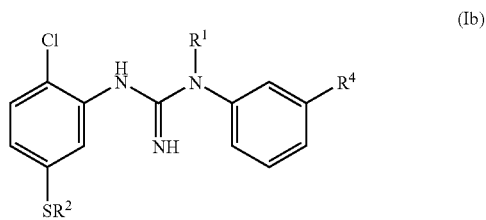

(Ib)

or a salt or solvate thereof, wherein:
$R^4$ is $C_{1-4}$ alkylthio, preferably —$SCH_3$;
$R^1$ is either —$^{11}CH_3$, —$^{11}CH_2CH_3$, or —$^{11}CH_2CH_2CH_3$ (preferably —$^{11}CH_3$), or $R^1$ is —$CH_2^{18}F$, —$CH_2CH_2^{18}F$, or —$CH_2CH_2CH_2^{18}F$ (preferably —$CH_2^{18}F$).

Most preferred compounds of formula (I) include:
(N-(2-chloro-5-(methylthio)phenyl)-N'-methylthio)phenyl)-N'-[N-methyl-$^{11}C$]-methylguanidine; and
(N-(2-chloro-5-(methylthio)phenyl)-N'-(3-methylthio) phenyl)-N'-[$^{18}F$]-fluoromethylguanidine.

According to a further aspect of the present invention, there is provided a compound of formula (Ic):

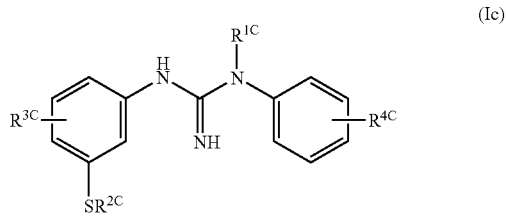

(Ic)

or a salt or solvate thereof, wherein:
$R^{1c}$ is $C_{1-4}$ alkyl or $C_{1-4}$ haloalkyl (preferably $C_{1-4}$ fluoroalkyl);
$R^{2c}$ is hydrogen or $C_{1-4}$ alkyl (preferably methyl);
$R^{3c}$ is radioiodine (suitably $^{123}I$, $^{124}I$, $^{125}I$, or $^{131}I$); and
$R^{4c}$ is halo, $C_{1-4}$ alkylthio, or $C_{1-4}$ alkyl.

In this aspect of the invention, $R^{3c}$ is preferably $^{124}I$ as this radioisotope has utility in PET.

Suitable salts according to the invention, include physiologically acceptable acid addition salts such as those derived from mineral acids, for example hydrochloric, hydrobromic, phosphoric, metaphosphoric, nitric and sulphuric acids, and those derived from organic acids, for example tartaric, trifluoroacetic, citric, malic, lactic, fumaric, benzoic, glycollic, gluconic, succinic, methanesulphonic, and para-toluenesulphonic acids.

As demonstrated below, the compounds of formula (I), (Ia), (Ib), and (Ic) have use as radioligands for the NMDA receptor. Therefore, according to a further aspect of the invention, there is provided a compound of formula (I), (Ia), (Ib), or (Ic) as defined above, or a salt or solvate thereof, for use in an in vivo diagnostic or imaging method such as PET. Suitably, a compound of formula (I), (Ia), (Ib), or (Ic) as defined above, or a salt or solvate thereof may be used to image the NMDA receptor in healthy human volunteers.

Suitably, the compounds of formula (I), (Ia), (Ib), or (Ic) or salt or solvate thereof are useful for in vivo imaging of NMDA receptors and thus have utility in the diagnosis of NMDA-mediated disorders, such as stroke, brain or spinal chord trauma, epilepsy, Alzheimer's disease, or Huntington's disease. Accordingly, there is further provided use of a compound of formula (I), (Ia), (Ib), or (Ic) or a salt or solvate thereof in the manufacture of a radiopharmaceutical for the in vivo diagnosis or imaging of an NMDA-mediated disease.

In the alternative, there is provided a method for the in vivo diagnosis or imaging of NMDA-mediated disease in a subject, preferably a human, comprising administration of a compound of formula (I), (Ia), (Ib), or (Ic) or a salt or solvate thereof. The method is especially preferred for the in vivo diagnosis or imaging of stroke, brain or spinal chord trauma, epilepsy, Alzheimer's disease, or Huntington's disease.

A compound of formula (I), (Ia), (Ib), (Ic) or a salt thereof is preferably administered in a radiopharmaceutical formulation comprising the compound of the invention. A "radiopharmaceutcal formulation" is defined in the present invention as a formulation comprising compound of formula (I) or a salt thereof in a form suitable for administration to humans. Administration is preferably carried out by injection of the formulation as an aqueous solution. Such a formulation may optionally contain further ingredients such as buffers; pharmaceutically acceptable solubilisers (e.g. cyclodextrins or surfactants such as Pluronic, Tween or phospholipids); pharmaceutically acceptable stabilisers or antioxidants (such as ascorbic acid, gentisic acid or para-aminobenzoic acid).

The dose of a compound of formula (I), (Ia), (Ib), (Ic) or a salt thereof will vary depending on the exact compound to be administered, the weight of the patient, and other variables as would be apparent to a physician skilled in the art. Generally, the dose would lie in the range 0.1 nmol/kg to 50 nmol/kg, preferably 1 nmol/kg to 5 nmol/kg.

A compound of formula (I), (Ia), or (Ib) or a salt or solvate thereof may be prepared from the corresponding compound of formula (II):

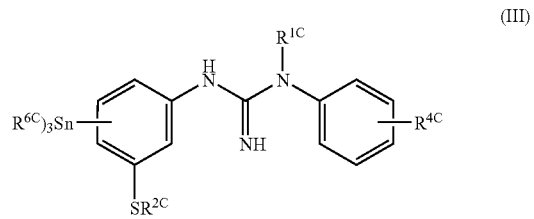

(II)

wherein $R^2$, $R^3$, and $R^4$ are as defined for the compound of formula (I), (Ia), or (Ib), by reaction with the appropriate alkylhalide X—$^{11}$CH$_2$R$^5$ or [$^{18}$F]—C$_{1-4}$fluoroalkyl Y wherein $R^5$ is as defined in formula (I), X is halo preferably iodo, and Y is halo, preferably chloro or bromo.

This reaction is preferably carried out in a polar aprotic solvent such as N,N-dimethylformamide (DMF) or acetonitrile and in the presence of a base, suitably an inorganic base such as potassium carbonate, potassium hydroxide, or sodium hydride, or an organic base such as a trialkylamine, for example triethylamine or diisopropylethylamine.

Alternatively, compounds of formula (I) in which $R^1$ is [$^{18}$F]—C$_{1-4}$ fluoroalkyl may be prepared from the corresponding precursor in which the group $R^1$ contains a leaving group such as mesylate, tosylate, triflate, nonaflate or halo and can be reacted with [$^{18}$F]— fluoride to give the desired compound of formula (I).

Compounds of formula (II) may be prepared as described in WO 94/27591 or Hu et al, J.Med. Chem. (1997), 40, 4281-9.

A compound of formula (Ic) or a salt or solvate thereof may be prepared from the is corresponding compound of formula (III):

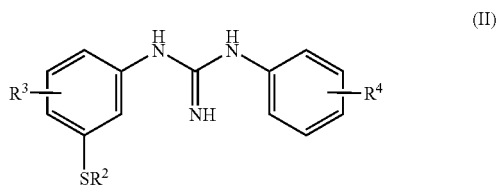

(III)

wherein $R^{1c}$, $R^{2c}$, and $R^{4c}$ are as defined for the compound of (Ic) and $R^{6c}$ is C$_{1-4}$ alkyl preferably n-butyl, by reaction with an appropriate labelled iodide salt, suitably and alkali metal iodide such as sodium iodide in the presence of an acid such as peracetic acid.

Compounds of formula (Ill) may be prepared according to Scheme 1:

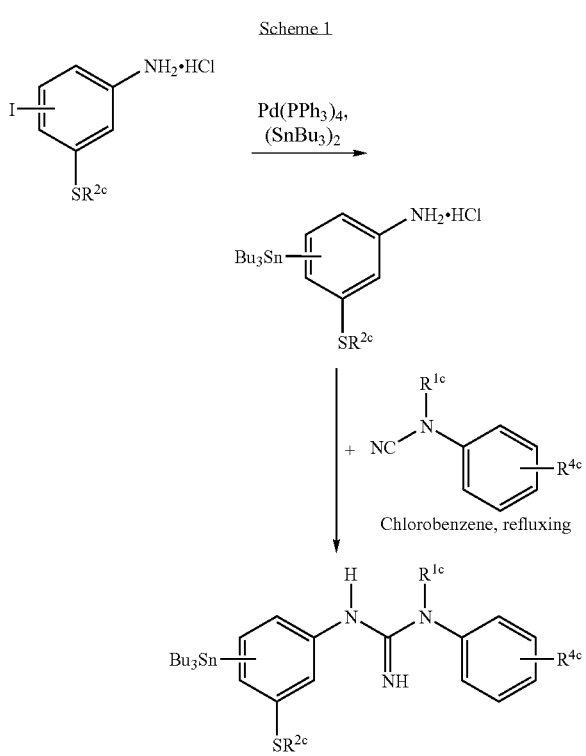

wherein $R^{1c}$, $R^{2c}$, and $R^{4c}$ are as defined for the compound of formula (III).

The invention will now be illustrated by way of the following Examples:

EXAMPLE 1

Synthesis of (N-(2-chloro-5-(methylthio)phenyl)-N'-(3-methylthio)phenyl)-N'-[N-methyl-$^{11}$C]-methylguanidine ("Compound 1")

(i) 2-chloro-5-(methylthio)aniline hydrochloride

To a stirred solution of 2-chloro-5-(methylthio)benzoic acid (5 g, 24.67 mmol) in t-butanol (20 mL) was added triethylamine (5.25 mL, 37.8 mmol). After stirring briefly, diphenylphosphoryl azide (6 mL, 27.60 mmol) was added dropwise. The reaction mixture was slowly heated to reflux for 6 hours and then cooled to room temperature. The solvent was removed under reduced pressure and the crude reaction mixture was dissolved in tetrahydrofuran (12.5 mL) followed by the addition of 12.5 mL trifluoroacetic acid (1:1). The reaction mixture was heated to reflux for 6 hours and the solvent was evaporated after cooling to room temperature. The reaction miture was treated with NaOH (25%) to bring the pH to 12 while cooling in an ice water bath. The product was repeatedly extracted into ethylacetate (4×25 mL) and the organic layer washed with water (10 mL). The combined extracts were dried over $MgSO_4$ and concentrated in vacuo to afford yellow oil. The product was purified by column chromatography ($SiO_2$, gradient of hexanes/EtOAc) and the collected samples dissolved in ether and treated with HCl/ether (10 mL, 1 M) to provide white crystals. The final product was a white solid (3.73 g, 87% yield): mp: 180-181° C.;

TLC: hexanes/EtOAc (9:1) $R_f$=0.51;

MS (Cl) m/e 174 (M+1 for $C_7H_8ClNS$) and m/e 191 ($M+NH_3$);

$^1$H-NMR (DMSO-$d_6$) δ (ppm)7.2-6.7 (m, 3H, Ar—H), 6.1 (br.s 2H, $NH_2$), 2.5 (s, 3H, S—$CH_3$);

$^{13}$C-NMR (DMSO-$d_6$) δ (ppm) 138.1 (C—$NH_2$, C1), 129.7 (C—S—$CH_3$, C5, and C—H, C3), 119.8 (C—H, C4), 118.1 (C—Cl, C2), 116.6 (C—H, C6), 14.6 (S—$CH_3$, C7);

IR: 3481.3 $cm^{-1}$ ($NH_2$), 2600-3000 $cm^{-1}$ (C—H aromatic, C—H aliphatic stretch), 1480-1600 $cm^{-1}$ (C=C), 1250 $cm^{-1}$ (S—$CH_3$), 1116 $cm^{-1}$ (C—N), 832 $cm^{-1}$ (C—H aromatic).

(ii) 3-(methylthio)phenylcyanamide

A solution of cyanogen bromide (1.42 g, 13.4 mmol) in anhydrous diethyl ether (8 mL) was added slowly to a stirred solution of 3-(methylthio)aniline (2.72 mL, 21.4 mmol) in anhydrous diethyl ether at 4° C. After the addition, the reaction mixture was stirred at 24° C. for 12 hours and became a brown solution with a white precipitate. The precipitate was filtered off; the filtrate was washed with aqueous HCl (1 M, 3×15 mL) in ether and the organic layer extracted with brine (10 mL). Then the ether solution was dried over $MgSO_4$, filtered, and concentrated in vacuo to yield a thick liquid. The crude product was further purified by column chromatography ($SiO_2$, a gradient of hexanes/$CH_2Cl_2$/EtOAc) to afford 3-(methylthio)phenyl cyanamide (0.7 g, 49% yield) as a white solid: m.p. 64-65° C.;

TLC dichloromethane/EtOAc (93:7) $R_f$=0.54;

MS (Cl) m/e 165 (M+1 for $C_8H_8N_2S$), 182 ($M+NH_4$), 199 ($M+NH_4+NH_3$), 216 ($M+NH_4+NH_3+NH_3$);

$^1$H-NMR ($CDCl_3$) δ (ppm) 7.2-6.7 (m, 4H, Ar—H), 7.5 (br.s, 1H, NH), 2.45 (s, 3H, S—$CH_3$);

$^{13}$C-NMR ($CDCl_3$) δ (ppm) 140.8 (C—NH, C1), 137.9 (C—$SCH_3$, C3), 129.9 (C—H, C5),121.3 (C—H, C2),112.9 (C—H, C4), 112.1 (C—H, C6), 111.6 (CN, C7), 15.5 (S—$CH_3$, C8);

IR: 3050-3172 $cm^{-1}$ (C—H aromatic stretch), 2900-3000 $cm^{-1}$ (C—H stretch, methyl C—H stretch), 2227 $cm^{-1}$ (CN), 1480-1600 $cm^{-1}$ (C=C), 1280-1350 $cm^{-1}$ (S—$CH_3$), 700-800 $cm^{-1}$ (C—H aromatic), 600 $cm^{-1}$ (C—S stretch).

(iii) N-(2-chloro-5-(methylthio)phenyl)-N'-(methylthio)phenyl)-guanidine

Aluminium chloride (0.67 g, 5 mmol) was added to a stirred solution of 3-(methylthio) phenylcyanamide (prepared using methods described in Example 1 (ii)) (0.82 g, 5 mmol) in chlorobenzene (8 mL) at 25° C. The solution was stirred for 5 min followed by the addition of 2-chloro-5-(methylthio)aniline hydrochloride (prepared using methods described in Example 1 (i)) (1.25 g, 6 mmol).The mixture was heated at 120-130° C. for 6 hours. The reaction mixture was cooled to room temperature and TLC showed that the reaction was completed. The crude product was then filtered, concentrated and then taken by dichloromethane, the resulting solution was washed by 1 M aqueous HCl and followed by saline. Afterwards, the crude product was dried over $MgSO_4$, filtered, and concentrated in vacuo to yield a thick liquid. The crude product was further purified by column chromatography ($SiO_2$, a gradient of $CH_2Cl_2$tMeOH) to afford 1.1 g N-(2-chloro-5-(methylthio)phenyl)-N'-(methylthioyphenyl) guanidine, yield 65%.

TLC: $CH_2Cl_2$/MeOH (9:1), $R_f$=0.36;

MS (Cl) m/e 338 ($M^+$+1 for $C_{15}H_{16}N_3S_2Cl$).

(iv) [N-methyl-$^{11}$C]-(N-(2-chloro-5-(methylthio)phenyl)-N'-(3-methylthio)phenyl)-N'-methylguanidine

[$^{11}$C] Iodomethane produced from the [$^{11}$C] $CO_2$ reaction with $LiAlH_4$ and HI was distilled into a reaction vial containing the 0.5 mg (1.5 μmol) precursor, N-(2-chloro-5-(methylthio)phenyl)-N'-(methylthio)phenyl)guanidine (prepared using methods described in Example 1 (iii)) in 250 μml acetonitrile and 0.6 mg sodium hydride (1 mg of 60% NaH dispersion in mineral oil, 25 μmol of NaH). The reaction was carried out at 65° C. with stirring for 5 minutes and final mixture was directly injected on to a μ-Bondapak C-18 column (7.8×300 mm) with a mobile phase of 70%acetonitrile/0.05M ammonium hydrogen phosphate (pH=8.39) at a flow rate of 2.5 ml/min and λ=254 nm. The radioactive peak eluted at 12.36 minutes.

EXAMPLE 2

Synthesis of (N-(2chloro-5-(methylthio)phenyl)-N'-(3-methylthio)phenyl)N'-[$^{18}$F]-fluoromethylquanidine

[$^{18}$F]Fluorobromomethane was prepared from dibromomethane via a nucleophilic substitution reaction using [$^{18}$F] fluoride. Purified from its precursor and solvent mixture by using a silica gel (70-230 mesh) packed column heated at 100° C., [$^{18}$F]Fluorobromomethane was trapped into a vial containing 1 mg of precursor (N-(2-chloro-5-(methylthio) phenyl)-N'-3-methylthio)phenyl)guanidine), 1 mg of sodium hydride and 0.5 ml of acetonitrile. After trapping, the mixture was allowed to stand at room temperature for 5-10 min for alkylation to complete. The final mixture was directly injected on to C-18 μ-BondaPak column (7.8×300 mm) with a mobile phase of 70% acetonitrile/30% 0.05M $(NH_4)_2HPO_4$ (pH=8.39) at a flow rate of 4.0 ml/min and λ=254 nm. The radiolabelled product peak had a retention time of 5.0 min, identical to that of authentic non-radiolabelled product.

Biological Data

Figure 1B:
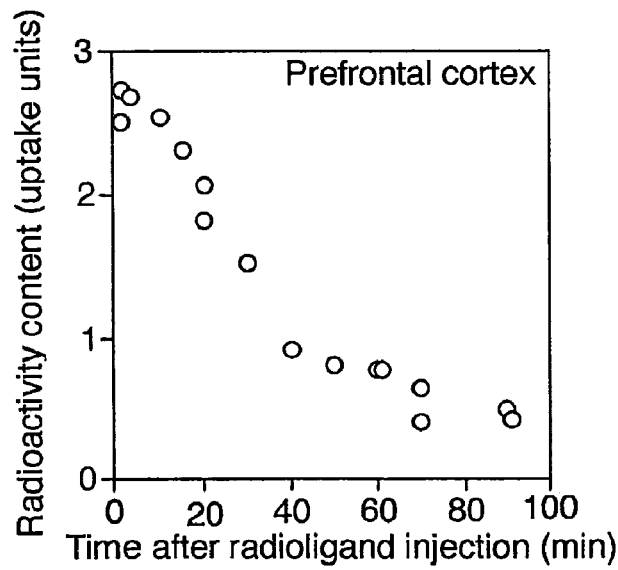
Figure 1C:
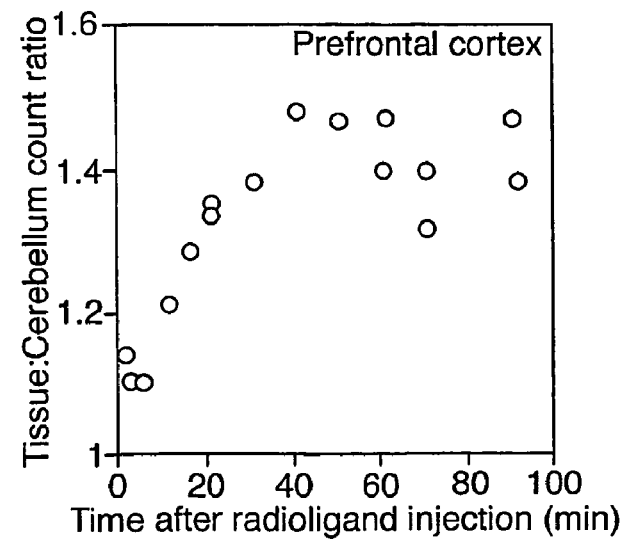

Biological data are presented with reference to the following FIG. 1 which shows radioactivity concentration (cpm/g tissue)/(injected cpm/g body weight) in two of the sampled brain tissues FIG. 1(a) cerebellum or FIG. 1(b) prefrontal cortex. In FIG. 1(c) the prefrontal cortex data are shown as ratios with the cerebellum data from individual rats, assuming the cerebellum to have low NMDA receptor density (Bowery et al, Br. J. Pharmacol. 93:944-954 (1988)).

Materials and Methods

Sixteen adult male Sprague-Dawley rats (body weight 250-320 g: mean±SD=288±25 g) were used in 5 separate experiments. Each rat was injected with ~13 MBq Compound 1, at a specific activity of 103±40 GBq/pmol, via a previously catheterised tail vein. The associated stable compound was 0.5±0.2 nmol/kg. Discrete samples of arterial blood were collected from 9 of the rats via a previously catheterised tail artery.

Biodistribution

Tissues were sampled post-mortem using an established protocol, as described in Hirani et al, Synapse 42:164-176 (2001). The radioactivity concentration data obtained at 12 times up to 90 min after radioligand injection were normalised for both amount injected and body weight, giving:— 'uptake units'=(cpm/g tissue)/(injected cpm/g body weight).

Metabolite Analysis

Plasma samples were injected directly onto a solid phase extraction (SPE) column (C18), with di-ammonium hydrogen phosphate (0.1 M) mobile phase, and the retained radioactivity subsequently injected onto a reverse phase HPLC column (300×7.8 mm i.d., p-Bondapak C18) with a mobile phase of methanol:0.1 M ammonium formate, 70:40 v/v. The eluates were monitored for radioactivity and absorbance at 254 nm. Brain tissues were assayed using the same methodology, excepting that the samples were homogenised and de-proteinated prior to injection onto the HPLC column.

Results

Blood and Plasma

Following the initial, rapid decrease in radioactivity concentration concomitant with the tissue distribution phase, the radioactivity level in both whole blood and plasma remained at ~0.2 uptake units for the period 5 to 90 min after intravenous injection. The percentage of radioactivity associated with parent decreased rapidly, to ~50% at 10 min and reached ~5% at 90 min.

Biodistribution

Brain.

Full data sets for each tissue sampled are given in Table 1. Following intravenous injection, there was a high extraction of radioactivity into the brain. All tissues showed a further, small increase in Compound 1 content within the first 5 minutes, followed by a gradual decrease. As a result of differential retention, slight heterogeneity in distribution developed over time. Highest radioactivity concentrations were measured in cortex and hippocampus with lowest values in medulla and cerebellum. The difference was maximal from 40 minutes after intravenous injection of the radioligand. In brain, Compound 1 represented approximately 95% and 90% of the radioactivity, at 20 and 70 minutes, respectively.

FIG. 1 illustrates uptake values in (a) cerebellum and (b) prefrontal cortex as a function of time after injection of Compound 1. Assuming that the radioactivity in cerebellum represents free and non-specifically bound Compound 1, FIG. 1(c) shows the development of 'specific signal' over the period of the experiment in cortex, with a final ratio of 'total'/'non-specific' of ~1.4.

Periphery.

The distribution of radioactivity in rat tissue as a function of time after intravenous injection of Compound 1 are presented in Table 2. The data are suitable for estimation of the Effective Dose Equivalent, for radiation dosimetry purposes.

Summary

Compound 1 showed rapid metabolism and clearance from the plasma with high extraction of the radiolabelled parent into rat brain. A specific signal (total/non-specific radioactivity) developed within a time commensurate with PET scanning. The signal was small but this might be expected in 'normal' brain, with a resting state of the NMDA receptor. If the specific signal represents selective binding to a site on the NMDA receptor, the signal should be increased following channel opening.

TABLE 1

Distribution of radioactivity in rat brain tissue as a function of time (minutes) after intravenous injection of Compound 1
Data are from 1 rat or 2 rats(*) per time point and are expressed in:-
Uptake Units = (cpm/g wet weight tissue)/(injected cpm/g body weight).

| Tissue | 1 | 2 | 5 | 10 | 15 | 20 | 30 | 40 | 50 | 60 | 70 | 90 min |
|---|---|---|---|---|---|---|---|---|---|---|---|---|
| Olfactory bulbs | 2.34 | 2.50 | 2.18 | 1.91 | 1.72 | 1.46 | 1.10 | 0.64 | 0.58 | 0.55* | 0.31 | 0.28* |
| Olfactory tubercles | 2.49 | 2.56 | 2.42 | 2.14 | 1.92 | 1.73 | 1.24 | 0.72 | 0.65 | 0.65* | 0.36 | 0.36* |
| Entorhinal cortex | 1.92 | 2.13 | 2.16 | 2.04 | 1.93 | 1.80 | 1.31 | 0.85 | 0.75 | 0.73* | 0.41 | 0.38* |
| Hypothalamus | 2.31 | 2.29 | 2.28 | 2.13 | 1.85 | 1.67 | 1.22 | 0.76 | 0.61 | 0.65* | 0.33 | 0.35* |
| Thalamus | 2.59 | 2.41 | 2.59 | 2.39 | 2.21 | 2.01 | 1.43 | 0.92 | 0.85 | 0.74* | 0.40 | 0.42* |
| Prefrontal cortex | 2.52 | 2.73 | 2.67 | 2.52 | 2.32 | 1.94* | 1.51 | 0.93 | 0.80 | 0.77* | 0.52* | 0.45* |
| Striata | 2.13 | 2.33 | 2.35 | 2.17 | 1.92 | 1.65* | 1.32 | 0.84 | 0.69 | 0.67* | 0.46* | 0.41* |
| Somatosensory cortex | 2.22 | 2.56 | 2.69 | 2.49 | 2.24 | 2.03 | 1.37 | 0.88 | 0.71 | 0.68* | 0.38 | 0.43* |
| Hippocampus | 1.61 | 1.73 | 2.00 | 1.81 | 1.74 | 1.60 | 1.32 | 0.86 | 0.73 | 0.76* | 0.54* | 0.46* |
| Visual cortex | 2.46 | 2.71 | 3.05 | 2.80 | 2.28 | 2.07 | 1.55 | 0.89 | 0.72 | 0.73* | 0.38 | 0.44* |
| Inferior colliculi | 3.42 | 3.65 | 3.23 | 2.69 | 2.22 | 1.97 | 1.16 | 0.64 | 0.56 | 0.54* | 0.39 | 0.36 |
| Superior colliculi | 2.42 | 2.64 | 2.59 | 2.35 | 2.01 | 1.64 | 1.19 | 0.65 | 0.57 | 0.54* | 0.28 | 0.23 |
| Medulla with Pons | 2.18 | 2.35 | 2.34 | 2.26 | 1.92 | 1.68 | 1.26 | 0.80 | 0.70 | 0.67* | 0.39 | 0.39* |
| Cerebellum | 2.21 | 2.47 | 2.43 | 2.08 | 1.81 | 1.45* | 0.55 | 0.62 | 0.55 | 0.54* | 0.38* | 0.32* |

TABLE 2

Distribution of radioactivity in rat tissue as a function of time (minutes) after intravenous injection of Compound 1
Tissue data are from 1 rat or 2 rats(*) per time point. Blood data are from a composite curve derived from 9 of the rats. Data are expressed in Uptake Units = (cpm/g wet weight tissue)/(injected cpm/g body weight).

| Tissue | 1 | 2 | 5 | 10 | 15 | 20 | 30 | 40 | 50 | 60 | 70 | 90 min |
|---|---|---|---|---|---|---|---|---|---|---|---|---|
| Whole blood | 0.59 | 0.42 | 0.26 | 0.21 | 0.19 | 0.18 | 0.19 | 0.16 | 0.16 | 0.17 | 0.18 | 0.18 |
| Plasma | 0.51 | 0.37 | 0.24 | 0.19 | 0.17 | 0.17 | 0.18 | 0.16 | 0.17 | 0.18 | 0.20 | 0.21 |
| Skeletal muscle | 1.07 | 1.14 | 1.32 | 1.05 | 1.07 | 0.96* | 0.68 | 0.61 | 0.61 | 0.49* | 0.44* | 0.35* |
| Skin | 0.47 | 0.54 | 0.61 | 0.70 | 0.51 | 0.68* | 0.75 | 0.39 | 0.52 | 0.46* | 0.47* | 0.40* |
| Urine | — | — | 11.7 | 10.9 | 22.0 | 10.7* | 37.5 | 27.5 | 84.5 | 24.4* | 16.9* | 46.4* |
| Fat | 0.15 | 0.18 | 0.23 | 0.50 | 0.75 | 0.40* | 0.71 | 0.45 | 0.49 | 0.79* | 0.55* | 0.51* |
| Testis | 0.50 | 0.51 | 0.56 | 0.66 | 0.66 | 0.73* | 0.76 | 0.74 | 0.69 | 0.89* | 0.74* | 0.79* |
| Small intestine | 3.38 | 3.87 | 3.17 | 2.49 | 2.79 | 2.16* | 2.30 | 1.09 | 1.19 | 1.29* | 1.34* | 0.93* |
| Sm. intestine content | 4.96 | 5.62 | 6.84 | 5.31 | 9.63 | 6.08* | 7.14 | 3.68 | 4.03 | 6.08* | 5.41* | 3.66* |
| Large intestine | 2.71 | 3.11 | 2.73 | 1.92 | 1.65 | 1.27* | 1.11 | 0.66 | 0.76 | 1.03* | 0.76* | 0.61* |
| Lge. intestine content | 0.11 | 0.21 | 0.13 | 0.17 | 0.03 | 0.28* | 0.36 | 0.23 | 0.35 | 0.44* | 0.57* | 0.66* |
| Spleen | 3.04 | 2.65 | 3.85 | 4.31 | 4.46 | 3.26* | 4.75 | 2.83 | 2.95 | 2.98* | 2.97* | 2.07* |
| Liver | 2.48 | 1.65 | 2.95 | 4.38 | 6.87 | 6.47* | 7.84 | 5.76 | 5.01 | 5.73* | 6.02* | 3.85* |
| Kidney | 12.5 | 10.8 | 8.70 | 5.72 | 4.78 | 3.19* | 2.85 | 1.79 | 1.68 | 1.87* | 1.88* | 1.50* |
| Stomach | 1.60 | 1.49 | 1.26 | 0.82 | 2.07 | 0.67* | 1.07 | 0.45 | 0.32 | 0.66* | 0.96 | 0.34* |
| Lung | 56.4 | 44.5 | 38.7 | 35.3 | 10.7 | 14.0* | 7.48 | 3.99 | 5.30 | 4.10* | 4.62* | 2.62* |
| Heart (ventricle) | 10.4 | 8.20 | 4.27 | 2.20 | 1.63 | 1.10* | 0.99 | 0.63 | 0.50 | 0.59* | 0.52* | 0.40* |

The invention claimed is:

1. A compound of formula (I):

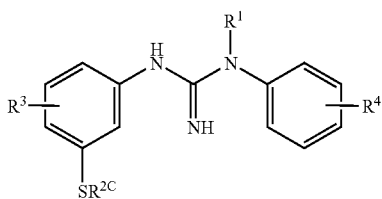

(I)

or a salt or solvate thereof, wherein:
R$^1$ is —$^{11}$CH$_2$R$^5$ or [$^{18}$F]—C$_{1-4}$ fluoroalkyl wherein R$^5$ is hydrogen or C$_{1-4}$ alkyl;
R$^2$ is hydrogen or C$_{1-4}$ alkyl;
R$^3$ is halo; and
R$^4$ is halo, C$_{1-4}$ alkylthio, or C$_{1-4}$ alkyl.

2. A compound according to claim 1 of formula (Ia):

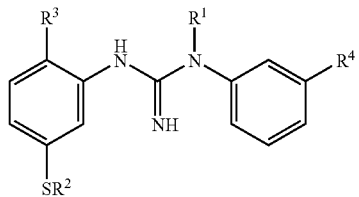

(Ia)

or a salt or solvate thereof, wherein R$^1$, R$^2$, R$^3$, and R$^4$ are as defined in claim 1.

3. A compound according to claim 1 of formula (Ib):

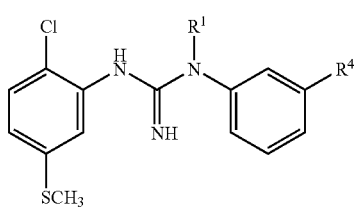

(Ib)

or a salt or solvate thereof, wherein:
R$^4$ is C$_{1-4}$ alkylthio;
R$^1$ is either —$^{11}$CH$_3$, —$^{11}$CH$_2$CH$_3$, or —$^{11}$CH$_2$CH$_2$CH$_3$ or R$^1$ is —CH$_2$$^{18}$F, —CH$_2$CH$_2$$^{18}$F, or —CH$_2$CH$_2$CH$_2$$^{18}$F.

4. A compound of formula (Ic):

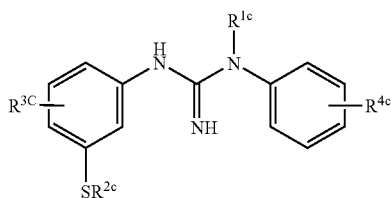

(Ic)

or a salt or solvate thereof, wherein:
R$^{1c}$ is C$_{1-4}$ alkyl or C$_{1-4}$ haloalkyl;
R$^{2c}$ is hydrogen or C$_{1-4}$ alkyl;
R$^{3c}$ is radioiodine (suitably $^{123}$I, $^{124}$I, $^{125}$I, or $^{131}$I); and
R$^{4c}$ is halo, C$_{1-4}$ alkylthio, or C$_{1-4}$ alkyl.

5. A compound according to claim 1, selected from:
(N-(2-chloro-5-(methylthio)phenyl)-N'-(3-methylthio)phenyl)-N'-[N-methyl-$^{11}$C]-methylguanidine; and
(N-(2-chloro-5-(methylthio)phenyl)-N'-(3-methylthio)phenyl)-N'-[$^{18}$F]-fluoromethylguanidine;
or a salt or solvate thereof.

6. A compound according to claim 1, for use in an in vivo diagnostic or imaging method such as PET.

7. A method for the in vivo diagnosis or imaging of NMDA-mediated disease in a subject, comprising administration of a compound according to claim 1.

* * * * *